(12) United States Patent
Ichikawa et al.

(10) Patent No.: US 10,918,744 B2
(45) Date of Patent: Feb. 16, 2021

(54) BIOMETRIC METHOD

(71) Applicants: Educational foundation Kyushu Bunka Gakuen, Nagasaki (JP); JAPAN REDOX LIMITED, Fukuoka (JP)

(72) Inventors: Kazuhiro Ichikawa, Nagasaki (JP); Tatsuya Naganuma, Fukuoka (JP)

(73) Assignees: Educational foundation Kyushu Bunka Gakuen, Nagasaki (JP); JAPAN REDOX LIMITED, Fukuoka (JP)

( * ) Notice: Subject to any disclaimer, the term of this patent is extended or adjusted under 35 U.S.C. 154(b) by 0 days.

(21) Appl. No.: 16/489,607

(22) PCT Filed: Mar. 1, 2017

(86) PCT No.: PCT/JP2017/008174
§ 371 (c)(1),
(2) Date: Aug. 28, 2019

(87) PCT Pub. No.: WO2018/158891
PCT Pub. Date: Sep. 7, 2018

(65) Prior Publication Data
US 2019/0388566 A1 Dec. 26, 2019

(51) Int. Cl.
*A61K 49/20* (2006.01)
*A61B 5/055* (2006.01)
(Continued)

(52) U.S. Cl.
CPC .............. *A61K 49/20* (2013.01); *A61B 5/055* (2013.01); *G01R 33/483* (2013.01); *G01R 33/60* (2013.01)

(58) Field of Classification Search
CPC ...... A61K 49/20; A61B 5/055; G01R 33/483; G01R 33/60
See application file for complete search history.

(56) References Cited

U.S. PATENT DOCUMENTS 5,818,230 A * 10/1998 Katz ................. G01R 33/4633
324/309
6,574,495 B1 * 6/2003 Golman ................ A61K 49/06
600/420
(Continued)

FOREIGN PATENT DOCUMENTS

| JP | 2006-204551 A | 8/2006 |
| JP | 2008-508267 A | 3/2008 |
| JP | 2009-518440 A | 5/2009 |
| JP | 2012-220269 A | 11/2012 |
| JP | 2013-504349 A | 2/2013 |
| JP | 5574386 B2 | 8/2014 |

OTHER PUBLICATIONS

International Search Report issued in PCT/JP2017/008174 dated May 23, 2017 with English Translation (5 pages).
(Continued)

*Primary Examiner* — Gregory H Curran
(74) *Attorney, Agent, or Firm* — Nakanishi IP Associates, LLC

(57) ABSTRACT

A biometric method includes: a step (1) for administering, to a target organism from the outside thereof, one of (i) a target molecule A having both an unpaired electron and a magnetic resonance nucleus having a gyromagnetic ratio smaller than the same of $^{19}F$, and (ii) a target molecule B and a radical molecule C, the target molecule B having no unpaired electron, and further having a magnetic resonance nucleus having a gyromagnetic ratio smaller than the same of $^{19}F$, the radical molecule C having an unpaired electron; and a step (2) for causing electron spin resonance in the unpaired electron of the target molecule A or the radical molecule C by irradiating electromagnetic waves to the target organism, subsequently triggering nuclear magnetic resonance in the magnetic resonance nucleus having a gyromagnetic ratio smaller than the same of $^{19}F$ in one of the target molecule A
(Continued)

and the target molecule B, and further, measuring nuclear magnetic resonance signals. The step (2) is carried out in a magnetic field having such an intensity that the nuclear magnetic resonance signals of the magnetic resonance nucleus in one of the target molecule A and the target molecule B are degenerated, the magnetic resonance nucleus having a gyromagnetic ratio smaller than the same of $^{19}$F. The biometric method makes it possible to measure low-sensitivity magnetic resonance nucleus such as $^{13}$C, $^{15}$N, and $^{31}$P, which are important nuclides present in organism, with performance equal to or over that of a high-field MRI device.

17 Claims, 4 Drawing Sheets

(51) Int. Cl.
    *G01R 33/483*     (2006.01)
    *G01R 33/60*     (2006.01)

(56) References Cited

U.S. PATENT DOCUMENTS

| | | |
|---|---|---|
| 8,532,740 B2 | 9/2013 | Ichikawa et al. |
| 2008/0284429 A1 | 11/2008 | Marcus et al. |
| 2009/0214432 A1 | 8/2009 | Thaning |
| 2012/0258050 A1 | 10/2012 | Chen et al. |

OTHER PUBLICATIONS

International Preliminary Report on Patentability issued in PCT/JP2017/008174 dated Sep. 3, 2019 with English Translation (9 pages).

Ramachandran Murugesan et al. Magnetic Resonance in Medicine, vol. 48, 2002, pp. 523-529.

Roschmann P., Medical Physics, vol. 14(No. 6), 922-931, Nov./Dec. 1987.

\* cited by examiner

BIOMETRIC METHOD

FIELD OF THE INVENTION

The present invention relates to a biometric method to be carried out through the use of an Overhauser-effect MRI (Magnetic Resonance Imaging) (hereinafter, referred to as "OMRI") device which provides images of functions and/or shapes of organisms by virtue of ESR (Electron Spin Resonance) and NMR (Nuclear Magnetic Resonance).

BACKGROUND ART

It is possible in nuclear magnetic resonance (NMR) to identify molecular species by detecting a resonance frequency unique to nuclear species and a minute structure which appears in a specific molecular structure. A sensitivity for detection is much dependent on nuclear species, and further on an amount of existing molecular species. In conventional biometric measurement by virtue of NMR, $^1H$ contained in molecules of organism was attempted to detect. This is because $^1H$ exists so much in organism, and nucleus of $^1H$ has high sensitivity. With respect to $^{19}F$, since $^{19}F$ has high sensitivity relative to $^1H$, an attempt was made to measure $^{19}F$ by virtue of NMR (see the non-patent document 1).

In contrast, important nuclear species other than $^1H$, such as $^{13}C$, $^{15}N$ and $^{31}P$, has relative sensitivity much smaller per a single nucleus than the same of $^1H$. Accordingly, it is necessary to prepare an NMR/MRI device capable of generating a magnetic field having an intensity equal to or greater than ten or slightly more T, in order to measure magnetic resonance nucleus having low sensitivity, such as $^{13}C$, $^{15}N$ and $^{31}P$.

There is known a method, as a method for improving sensitivity to detect nuclear spin by virtue of a nuclear magnetic resonance process, for causing deviation in nuclear spin distribution (Dynamic Nuclear Polarization: DNP) to nearby magnetic resonance nucleus by virtue of electron-nucleus interaction, by causing electron spin resonance in molecules each having an unpaired electron. OMRI improves sensitivity for detecting $^1H$ (water molecule) in organism by virtue of the above-mentioned DNP. However, a distance by which electromagnetic wave can reach in organism is dependent on a frequency. Specifically, the higher a frequency of electromagnetic wave is, the shorter a distance by which electromagnetic wave can reach in organism is (see non-patent document 2). Since a frequency for exciting electrons is too high in a magnetic field having an intensity equal to or greater than tens of mT, a distance by which electromagnetic wave can reach into organism is short, and accordingly, it is not possible to actually cause electron spin resonance in organism. That is, an existing NMR/MRI providing a magnetic field having an intensity equal to or greater than tens of mT cannot be applied, just as it is, to OMRI.

Furthermore, as a method making use of DNP, there is also known a method for administering molecules in which nuclear spin is hyperpolarized at an extremely low temperature equal to or lower than 100 degrees Kelvin, into organism. However, this method needs ultra-low temperature atmosphere. Furthermore, it is necessary to carry out measurement before the condition of hyperpolarization of nuclear spin is relaxed, and then, is returned back to thermal equilibrium. Thus, the method merely provides data for a short period of time just after molecules in which nuclear spin was hyperpolarized have been administered into organism.

The applicants of the present invention have suggested a biometric apparatus for providing images of organism structure by applying various magnetic resonance such as electron spin resonance and nuclear magnetic resonance to water molecules existing in the organism (for instance, see the patent documents 1 and 2). The biometric apparatus includes a first magnetic field generator for generating a magnetic field having a predetermined intensity, and a second magnetic field generator for generating a magnetic field having an intensity greater than the intensity of the magnetic field generated by the first magnetic field generator. A target is moved in the first magnetic field generator and subsequently in the second magnetic field generator, resulting in that electron spin is excited by the first magnetic field generator generating a magnetic field having a lower intensity, and thereafter, OMRI measurement is carried out by the second magnetic field generator generating a magnetic field having a higher intensity, ensuring that external magnetic field around OMRI is extremely high, and accordingly, it is possible to obtain OMRI images having high sensitivity and high resolution.

PRIOR ART DOCUMENTS

Patent Documents

Patent document 1: Japanese Patent Application Publication No. 2006-204551
Patent document 2: Japanese Patent No. 5574386

Non-Patent Documents

Non-patent document 1: Ramachandran Murugesan, Sean English, Koen Reijnders, Ken-ichi Yamada, John A. Cook, James B. Mitchell, Snkaran Subramanian, and Murali C. Krishna, Fluorine Electron Double Resonance Imaging for $^{19}F$ MRI in Low Magnetic Fields, Magnetic Resonance in Medicine, Volume 48, 2002, pp 523-529
Non-patent document 2: Roschmann P., Radiofrequency penetration and absorption the human body: Limitations to high-field whole-body nuclear magnetic resonance imaging, Med. Phys., 14(6), 922, 1987

DISCLOSURE OF THE INVENTION

Problems to be Solved by the Invention

As mentioned before, it is necessary to make a magnetic field having an intensity equal to or greater than ten or slightly more T in order to measure magnetic resonance nucleus having low sensitivity, such as $^{13}C$, $^{15}N$ and $^{31}P$, which are important nuclear species other than $^1H$. However, it is quite difficult to prepare an NMR/MRI device capable of generating a magnetic field having a requisite high intensity. Furthermore, OMRI is restricted on a frequency for exciting electrons in relation with a distance by which electromagnetic wave can penetrate organism, and accordingly, it is not possible to apply an NMR/MRI device capable of generating a magnetic field having a requisite high intensity, as it is, to OMRI. Thus, those skilled in the art understand that it is naturally impossible to carry out OMRI to magnetic resonance nucleus at low sensitivity in organism.

Under the above-mentioned circumstance, it is an object of the present invention to provide a biometric method making it possible to measure low-sensitivity magnetic resonance nucleus such as $^{13}C$, $^{15}N$, and $^{31}P$, which are important nuclides present in organism, with performance equal to or over that of a high-field NMR/MRI device, though such measurement was conventionally considered impossible.

Solution to the Problems

With the study and research by the inventors for solving the above-mentioned problem, the inventors have found that it was possible to improve sensitivity for detection by accomplishing hyperpolarization by virtue of Overhauser-effect, and further, degenerating nuclear magnetic resonance signals, even if nucleus existing in organism had a small gyromagnetic ratio. The inventors have further found that the invention identified below meets with the above-mentioned object, and thus, reached the present invention.

That is, the present invention is identified as follows.

<1> A biometric method including a step (1) for administering, to a target organism from the outside thereof, one of (i) a target molecule A having both an unpaired electron and a magnetic resonance nucleus having a gyromagnetic ratio smaller than the same of $^{19}F$, and (ii) a target molecule B and a radical molecule C, the target molecule B having no unpaired electron, and further having a magnetic resonance nucleus having a gyromagnetic ratio smaller than the same of $^{19}F$, the radical molecule C having an unpaired electron, and a step (2) for causing electron spin resonance in the unpaired electron of the target molecule A or the radical molecule C by irradiating electromagnetic waves to the target organism through an Overhauser-effect MRI device, subsequently triggering nuclear magnetic resonance in the magnetic resonance nucleus having a gyromagnetic ratio smaller than the same of $^{19}F$ in one of the target molecule A and the target molecule B, and further, measuring nuclear magnetic resonance signals, the step (2) being carried out in a magnetic field having such an intensity that the nuclear magnetic resonance signals of the magnetic resonance nucleus in one of the target molecule A and the target molecule B are degenerated, the magnetic resonance nucleus having a gyromagnetic ratio smaller than the same of $^{19}F$.

<2> The biometric method as set forth in <1>, wherein a molecule administered to the target organism from the outside in the step (1) is (i) a target molecule A having both an unpaired electron and a magnetic resonance nucleus having a gyromagnetic ratio smaller than the same of $^{19}F$.

<3> The biometric method as set forth in <1>, wherein a molecule administered to the target organism from the outside in the step (1) is (ii) a target molecule B and a radical molecule C, the target molecule B having no unpaired electron, and further having a magnetic resonance nucleus having a gyromagnetic ratio smaller than the same of $^{19}F$, the radical molecule C having an unpaired electron.

<4> The biometric method as set forth in any one of <1> to <3>, wherein the magnetic resonance nucleus comprises one of $^{13}C$, $^{14}N$, $^{15}N$, and $^{31}P$.

<5> The biometric method as set forth in <4>, wherein the magnetic resonance nucleus comprises $^{13}C$.

<6> The biometric method as set forth in any one of <1> to <5>, wherein the step (2) is carried out in a magnetic field having an intensity equal to or smaller than 50 mT.

<7> The biometric method as set forth in any one of <1> to <6>, wherein the step (2) is carried out in a magnetic field having a constant intensity.

<8> The biometric method as set forth in any one of <1> to <7>, wherein one of the target molecule A and the target molecule B includes two or more magnetic resonance nuclei having a gyromagnetic ratio smaller than the same of $^{19}F$.

<9> The biometric method as set forth in any one of <1> to <8>, wherein one of the target molecule A and the target molecule B has accumulation characteristics to tumor.

<10> The biometric method as set forth in any one of <1> to <9>, wherein one of the target molecule A and the target molecule B comprises glucose derivative.

<X1> A diagnostic method to be carried out making use of the method as set forth in any one of <1> to <10>.

The present invention further provides a biometric apparatus including a first device for administering, to a target organism from the outside thereof, one of (i) a target molecule A having both an unpaired electron and a magnetic resonance nucleus having a gyromagnetic ratio smaller than the same of $^{19}F$, and (ii) a target molecule B and a radical molecule C, the target molecule B having no unpaired electron, and further having a magnetic resonance nucleus having a gyromagnetic ratio smaller than the same of $^{19}F$, the radical molecule C having an unpaired electron, and a second device for causing electron spin resonance in the unpaired electron of the target molecule A or the radical molecule C by irradiating electromagnetic waves to the target organism, subsequently triggering nuclear magnetic resonance in the magnetic resonance nucleus having a gyromagnetic ratio smaller than the same of $^{19}F$ in one of the target molecule A and the target molecule B, and further, measuring nuclear magnetic resonance signals, the second device measuring the nuclear magnetic resonance signals in a magnetic field having such an intensity that the nuclear magnetic resonance signals of the magnetic resonance nucleus in one of the target molecule A and the target molecule B are degenerated, the magnetic resonance nucleus having a gyromagnetic ratio smaller than the same of $^{19}F$.

The present invention further provides a recording medium readable by a computer, storing a program therein for causing a computer to carry out the above-mentioned biometric method in a biometric apparatus.

Advantages Provided by the Invention

The present invention provides a biometric method making it possible to measure low-sensitivity magnetic resonance nucleus such as $^{13}C$, $^{15}N$, and $^{31}P$, which are important nuclides existing in organism, with performance equal to or over that of a high-field NMR/MRI device, although such measurement was conventionally considered impossible.

INDICATION BY REFERENCE NUMERALS

Figure 1:
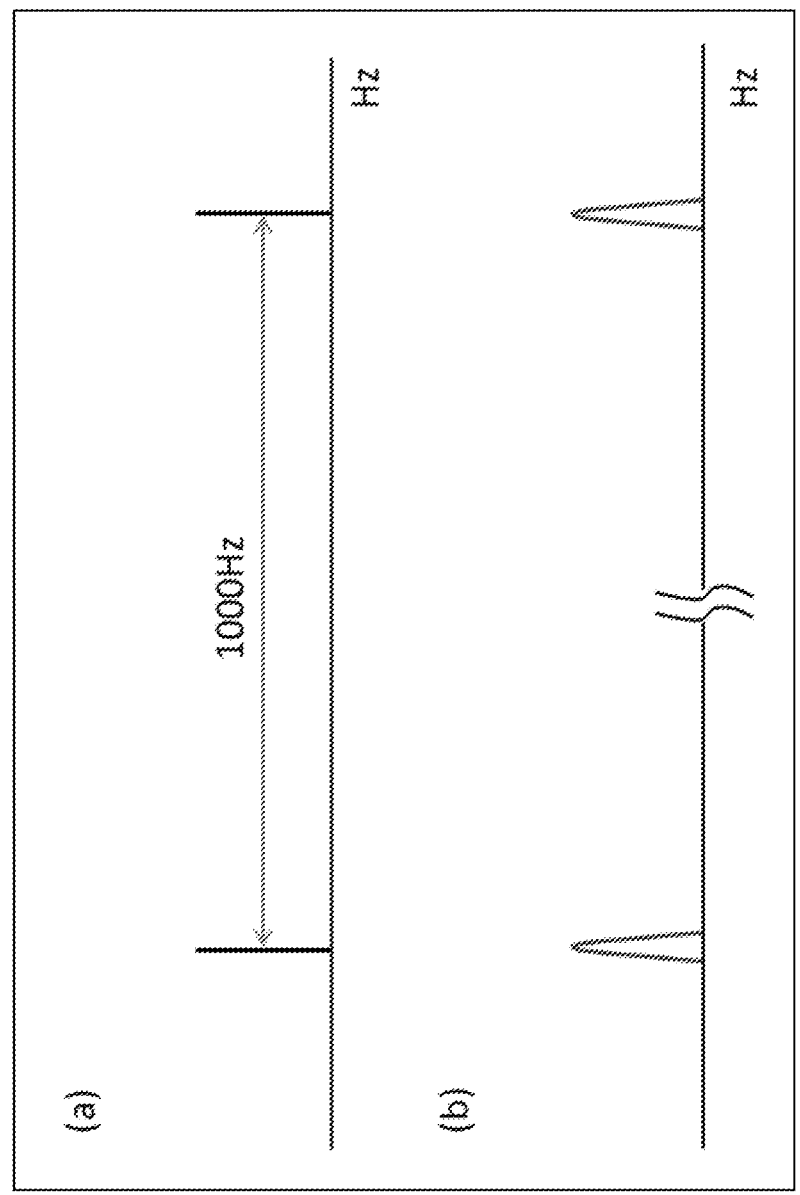
FIG. 1 includes schematic views of $^{13}C$-NMR spectrum (9.4 T and comparison) to be used for explaining degeneration of nuclear magnetic resonance signals.

10 OMRI apparatus
11 Main part 111 external magnetic field generator
111x eternal magnet
111y Magnetic field gradient coil
111z Magnetic field sweep coil
112 RF coil (resonator)
113 Fixation stand
114 Driver for generating static magnetic field
115 RF coil driver
116 Detection signal receiver
12 Controller
121 Measurement sequence processor
122 OMRI measurement processor
124 Detection signal adjuster
13 Display
M Mouse

EMBODIMENTS FOR REDUCING THE INVENTION TO PRACTICE

Preferred embodiments in accordance with the present invention will be explained hereinbelow in detail. However, it should be noted that elements described hereinbelow are just examples (typical examples) of the embodiment in accordance with the present invention, and that the scope of the present invention is not to be limited to a scope mentioned below unless the gist of the present invention is not changed.

Hereinbelow, in the specification, a target molecule A or a target molecule B may be referred to simply as "a target molecule", magnetic resonance nucleus having a gyromagnetic ratio smaller than the same of $^{19}F$ may be referred to simply as "a low gyromagnetic ratio nucleus", and a nuclear magnetic resonance signal may be referred to simply as "a signal".

The present invention provides a biometric method (hereinafter, referred to as "the biometric method in accordance with the present invention") including a step (1) for administering, to a target organism from the outside thereof, one of (i) a target molecule A having both an unpaired electron and a magnetic resonance nucleus having a gyromagnetic ratio smaller than the same of $^{19}F$, and (ii) a target molecule B and a radical molecule C, the target molecule B having no unpaired electron, and further having a magnetic resonance nucleus having a gyromagnetic ratio smaller than the same of $^{19}F$, the radical molecule C having an unpaired electron, and a step (2) for causing electron spin resonance in the unpaired electron of the target molecule A or the radical molecule C by irradiating electromagnetic waves to the target organism through an Overhauser-effect MRI device, subsequently triggering nuclear magnetic resonance in the magnetic resonance nucleus having a gyromagnetic ratio smaller than the same of $^{19}F$ in one of the target molecule A and the target molecule B, and further, measuring nuclear magnetic resonance signals, the step (2) being carried out in a magnetic field having such an intensity that the nuclear magnetic resonance signals of the magnetic resonance nucleus in one of the target molecule A and the target molecule B are degenerated, the magnetic resonance nucleus having a gyromagnetic ratio smaller than the same of $^{19}F$.

The present invention is partially characterized in that nuclear spin in a nucleus having a low gyromagnetic ratio (magnetic resonance nucleus having a gyromagnetic ratio smaller than the same of $^{19}F$) of the target molecule (the target molecule A or the target molecule B) is hyperpolarized in organism by virtue of Overhauser-effect.

That is, in the present invention, electromagnetic waves are irradiated from the outside to a target organism to which a target molecule A or both a target molecule B and a radical molecule C has been administered, to thereby cause electron spin resonance in an unpaired electron or unpaired electrons of the thus administered molecule A or radical molecule C. As a result, nuclear spin in the magnetic resonance nucleus is hyperpolarized by virtue of Overhauser-effect (interaction phenomenon between electron spin and nuclear spin) of both the excited electron spin and the nuclear spin in magnetic resonance nucleus, which has a gyromagnetic ratio smaller than the same of $^{19}F$, of the target molecule A or B. Consequently, nuclear magnetic resonance in the magnetic resonance nucleus can be measured with enhanced sensitivity in comparison with a case in which nucleus having a small gyromagnetic ratio in the target molecule is measured without accomplishing hyperpolarization.

Furthermore, it is not always necessary to carry out the step (2) immediately after the step (1) by accomplishing the above-mentioned hyperpolarization. There is known a conventional process, as a process making use of hyperpolarization, in which molecules in which nuclear spin is hyperpolarized at an ultra-low temperature are administered to organism. However, this conventional process is accompanied with a problem that the measurement has to be finished before the hyperpolarization condition of nuclear spin is relaxed, and then, returns back to thermal equilibrium. Thus, the conventional process merely provides data for a short period of time (about 1 minute) after molecules in which nuclear spin is hyperpolarized have been administered to organism. In contrast, the biometric method in accordance with the present invention makes it possible to accomplish hyperpolarization to nuclear spin in nucleus, which has a low gyromagnetic ratio, of the target molecule by virtue of the interaction phenomenon between electron spin and nuclear spin, even though a certain period of time has lapsed after the step (1) was carried out.

The present invention is further partially characterized in that an intensity of a magnetic field in the step (2) is set to such an intensity that nuclear magnetic resonance signals of nucleus, which has a low gyromagnetic ratio, of the target molecule are degenerated. By so setting a magnetic field intensity, it is possible to further intensify a signal intensity, ensuring that measurement sensitivity can be enhanced even though nucleus existing in organism has a low gyromagnetic ratio.

It should be noted that a magnetic field intensity referred to in the phrase "a magnetic field having such an intensity that the nuclear magnetic resonance signals of the magnetic resonance nucleus in one of the target molecule A and the target molecule B are degenerated, the magnetic resonance nucleus having a gyromagnetic ratio smaller than the same of $^{19}F$" is not always necessary to be equal to an intensity at which signals of all of nuclei, which have a low gyromagnetic ratio, of the target molecule A or B are degenerated. A necessary magnetic field intensity may be such an intensity that at least two signals among signals of nuclei, which have a low gyromagnetic ratio, of the target molecule A or B are degenerated.

The phrase "nuclear magnetic resonance signals are degenerated" means that two nuclear magnetic resonance signals overlap at least partially (two nuclear magnetic resonance signals are identical in at least a part of a frequency with each other) in at least two nuclear magnetic resonance signals. A signal intensity of degenerated signals is generally enhanced relative to a signal intensity of a single nuclear magnetic resonance signal.

In the biometric method in accordance with the present invention, it is also possible to regularly measure the target molecule. For instance, it is sometimes difficult to regularly carry out measurement in PET diagnosis, taking risk of radiation exposure into consideration, because the diagnosis is carried out by detecting radiation emitted out of molecules having been labelled with radiation isotope. In contrast, since the biometric method in accordance with the present invention makes use of electron spin resonance and nuclear magnetic resonance, the regular measurement exerts just a small influence to organism.

Hereinbelow are explained each of the steps defined in the biometric method in accordance with the present invention.

[Step (1)]

The step (1) in the biometric method in accordance with the present invention is defined as a step for administering (i) or (ii) identified below to a target organism from the outside thereof (i) a target molecule A having both an unpaired electron and a magnetic resonance nucleus having a gyromagnetic ratio smaller than the same of $^{19}F$.

(ii) a target molecule B and a radical molecule C, the target molecule B having no unpaired electron, and further having a magnetic resonance nucleus having a gyromagnetic ratio smaller than the same of $^{19}F$, the radical molecule C having an unpaired electron.

The biometric method in accordance with the present invention is applied to a human being. The biometric method in accordance with the present invention may be applied to, other than a human being, domestic animals such as cow, horse and pig, or animals such as monkey, marmot, rabbit, rat and mouse.

Magnetic resonance nucleus (nuclear species) to be measured in the present invention is magnetic resonance nucleus, which has a gyromagnetic ratio smaller than the same of $^{19}F$, existing in a target molecule of target organism (low gyromagnetic ratio nucleus). That is, magnetic resonance nucleus to be measured has a gyromagnetic ratio smaller than the same of $^{19}F$. It has been conventionally understood that low gyromagnetic ratio nucleus had low sensitivity, and accordingly, it was impossible to measure magnetic resonance of nucleus in organism.

However, as mentioned above, the biometric method in accordance with the present invention makes it possible to hyperpolarize nuclear spin of low gyromagnetic ratio nucleus in organism by virtue of Overhauser-effect, and carry out measurement at such a magnetic field intensity that nuclear magnetic resonance signals are degenerated. Thus, it is possible to measure the signals with and enhanced intensity and further with enhanced sensitivity.

Low gyromagnetic ratio nucleus to be measured is preferably selected from $^{13}C$, $^{14}N$, $^{15}N$ and $^{31}P$. Most preferable nucleus is $^{13}C$.

The target molecule A includes an unpaired electron, and further includes nuclear resonance nucleus having a gyromagnetic ratio smaller than the same of $^{19}F$. That is, the target molecule A is defined as a molecule causing both electron spin resonance and nuclear magnetic resonance. Accordingly, it is not necessary to administer a radical molecule to organism, but the target molecule A together with a radical molecule may be administered to organism.

The target molecule B does not include an unpaired electron, but includes magnetic resonance nucleus having a gyromagnetic ratio smaller than the same of $^{19}F$. That is, the target molecule B does not cause electron spin resonance (ESR), but causes nuclear magnetic resonance. Accordingly, the target molecule B is usually used together with the radical molecule C having an unpaired electron, but causing ESR.

The target molecule can be designed to have a structure selected, as long as the object of the present invention can be accomplished, in dependence on the object. The target molecule may be designed to include as a constituent part thereof a plurality of nuclei each having a low gyromagnetic ratio. Nucleus having a low gyromagnetic ratio may be selected in dependence on a purpose among a plurality of nuclei each having a low gyromagnetic ratio.

The target molecule usually includes two or more magnetic resonance nuclei each having a gyromagnetic ratio smaller than the same of $^{19}F$.

It is preferable that chemical shift values of nuclei each having a low gyromagnetic ratio and includes in the target molecule are almost equal to one another in order to further enhance an intensity of the signals. For instance, in the case that the target molecule includes two or more nuclei each having a low gyromagnetic ratio, it is preferable for the target molecule to have such a structure that a difference between a maximum and a minimum in chemical shift values of the nuclei is in the range of 1 to 50 ppm both inclusive.

When $^{13}C$ is to be measured as a nucleus having a low gyromagnetic ratio, two or more carbon atoms among carbon atoms defining the target molecule are labelled with $^{13}C$. A number of $^{13}C$ labels can be changed in line with a structure of the target molecule and/or a purpose, and may be three, four, five or six. Since a signal intensity to be measured increases in proportion with a number of $^{13}C$ labels, it is preferable that carbon atoms as much as possible are labelled with $^{13}C$ for further enhancing a signal intensity.

It is possible to select any target molecule in accordance with a purpose. For instance, a target molecule having accumulation characteristics to organ and tumor. By using a target molecule having accumulation characteristic to malignant tumor such as cancer, it is possible to know whether cancer exists or how cancer distributes in organism. As a molecule having accumulation characteristic to tumor, there may be used glucose or glucose derivatives, for instance.

Such target molecule can be used as a contrast agent for tumors, and the biometric method of the present invention may be applied to cancer diagnosis.

The radical molecule is defined as a molecule including an unpaired electron, and causing electron spin resonance. The radical molecule C may be selected in accordance with the target molecule B among chemicals having been conventionally used as radical probes. The target molecule B can be hyperpolarized more readily in a case that the target molecule B and the radical molecule C are situated close to each other in such a distance that electron spin in the radical molecule C and nuclear spin in a low gyromagnetic ratio nucleus of the target molecule B interact with each other. Accordingly, it is preferable that the target molecule B and the radical molecule C have almost same distribution in organism.

A process of administering the target molecule and the radical molecule C is not to be limited to any process, and may be selected as a process of administrating them into a blood vessel such as artery and vein, or a process of administering them through a mouth.

In one of examples of the step (1), (i) the target molecule A including an unpaired electron, and further including a magnetic resonance nucleus having a gyromagnetic ratio smaller than the same of $^{19}F$ is administered to a target organism from the outside thereof.

In this case, since electron spin excited by electron spin resonance (ESR) exists in the vicinity of magnetic resonance nucleus, nuclear spin can be readily hyperpolarized by virtue of interaction phenomenon between electron spin and nuclear spin (Overhauser-effect).

In another example of the step (1), (ii) the target molecule B and the radical molecule C are administered to a target organism from the outside thereof, in which case, the target molecule B has no unpaired electron, but includes a magnetic resonance nucleus having a gyromagnetic ratio smaller than the same of $^{19}$F, and the radical molecule C has an unpaired electron.

By separating a molecule in which electron spin resonance is caused from a molecule in which nuclear magnetic resonance is caused, a period of time for relaxation is prolonged, and hence, it is possible to extend a period of time for measurement, ensuring enhancement in sensitivity.

The target molecule A, the target molecule B and the radical molecule C to be administered into organism are not necessary to be a single kind of molecule. A plurality of the target molecule A, the target molecule B or the radical molecule C may be administered at a time into organism. Furthermore, target molecule A, and a combination of the target molecule B and the radical molecule C may be used together.

[Step (2)]

The step (2) is comprised of a step for causing electron spin resonance in the unpaired electron of the target molecule A or the radical molecule C by irradiating electromagnetic waves to the target organism through an Overhauser-effect MRI device, subsequently triggering nuclear magnetic resonance in the magnetic resonance nucleus having a gyromagnetic ratio smaller than the same of $^{19}$F in one of the target molecule A and the target molecule B, and further, measuring nuclear magnetic resonance signals, the measurement being to be carried out in a magnetic field having such an intensity that the nuclear magnetic resonance signals of the magnetic resonance nucleus in one of the target molecule A and the target molecule B are degenerated, the magnetic resonance nucleus having a gyromagnetic ratio smaller than the same of $^{19}$F.

In the step (2), electromagnetic waves (micro-waves) are irradiated to target organism to which (i) the target molecule A or (ii) the target molecule B and the radical molecule C have been administered to thereby cause electron spin resonance in the unpaired electron existing in the administered target molecule A or radical molecule C. That is, electron spin is excited in the unpaired electron present in the administered target molecule A or radical molecule C by irradiating electromagnetic waves to the target organism. Energy of the thus excited electron spin makes transition, by virtue of Overhauser-effect (interaction phenomenon between electron spin and nuclear spin), nuclear spin in a nucleus, having a low gyromagnetic ratio, of the target molecule A or B. Thus, the nuclear spin in the nucleus, having a low gyromagnetic ratio, of the target molecule A or B is hyperpolarized.

Then, nuclear magnetic resonance is caused in the low gyromagnetic ratio nucleus of the target molecule A or B to thereby measure the nuclear magnetic resonance signals. A magnetic field at which the nuclear magnetic resonance is to be measured is set to have such an intensity that signals of the low gyromagnetic ratio nuclei of the target molecule A or B to be measured overlap each other.

As mentioned above, an intensity of a magnetic field at which the step (2) is carried out is not always necessary to be an intensity at which signals of all of low gyromagnetic ratio nuclei existing in the target molecule A are degenerated. A necessary magnetic field intensity may be such an intensity that at least two signals among the signals of the low gyromagnetic ratio nuclei of the target molecule are degenerated.

A magnetic field intensity for causing electron spin resonance and a magnetic field intensity for causing nuclear magnetic resonance each may be set to any intensity as long as the object of the present invention can be accomplished. A magnetic field intensity at which the step (2) is to be carried out may be set to any intensity in dependence on a specific target molecule to be selected, for instance.

For instance, the magnetic field intensity may be designed to be such an intensity that nuclear magnetic resonance signals of two or more (preferably, three or more) low gyromagnetic ratio nuclei of the target molecule may be compressed into a 5 Hz frequency band, a 10 Hz frequency band, a 15 Hz frequency band, or a 20 Hz frequency band.

The step (2) is usually carried out keeping a magnetic field intensity constant. That is, a magnetic field intensity for causing electron spin resonance is substantially equal to a magnetic field intensity for causing nuclear magnetic resonance.

By keeping a magnetic field intensity constant in the step (2), it is possible to measure electron spin resonance and nuclear magnetic resonance with a common magnet. Hence, since it is not necessary to separately use two magnets to measure electron spin resonance and nuclear magnetic resonance, it is possible to measure nuclear magnetic resonance immediately after the measurement of electron spin resonance, ensuring that the measurement is hardly influenced by the relaxation. Furthermore, it is also an advantage to be able to prevent the apparatus from increasing in size, and to be unnecessary to move target organism.

It is preferable that the step (2) is carried out at a magnetic field intensity equal to or smaller than 50 mT. By so setting a magnetic field intensity, nuclear magnetic resonance signals can be readily degenerated.

A lower limit of a magnetic field intensity is not to be limited to any intensity as long as the object of the present invention is not impeded. For instance, the lower limit may be set equal to or greater than 10 mT or 20 mT.

In contrast, a magnetic field intensity for causing electron spin resonance and a magnetic field intensity for causing nuclear magnetic resonance may be different from each other. In the case that a magnetic field intensity for causing electron spin resonance and a magnetic field intensity for causing nuclear magnetic resonance is different from each other, it is preferable that a magnetic field intensity for causing electron spin resonance is equal to or smaller than 50 mT, and further, a magnetic field intensity for causing nuclear magnetic resonance is equal to or smaller than 50 mT.

A period of time before nuclear magnetic resonance is caused after electron spin was excited is not to be limited to any specific period of time, if the electron spin is excited before the hyperpolarized nuclear spin returns back to thermal equilibrium, and magnetization amplification is lost. A velocity at which hyperpolarized nuclear spin returns back to thermal equilibrium and the amplification is lost is dependent on a kind of a low gyromagnetic ratio nucleus and an atmosphere in which a target molecule is measured (such as solvent). Consequently, a period of time before nuclear magnetic resonance is caused after electron spin was excited is determined in accordance with a kind of a low gyromagnetic ratio nucleus and an atmosphere in which a target molecule is measured (such as solvent).

For instance, in the case that the target molecule includes $^{13}$C as a nucleus having a low gyromagnetic ratio, a period of time in which nuclear spin having been hyperpolarized returns back to thermal equilibrium, and magnetization amplification is lost is in the range of a few seconds to hundreds of seconds. Consequently, in the case that the target molecule includes $^{13}C$ as a nucleus having a low gyromagnetic ratio, it is possible to almost ignore magnetization loss by setting a period of time for causing nuclear magnetic resonance after electron spin was excited, to be equal to or smaller than tens of seconds (for instance, equal to or smaller than 10 seconds).

In the biometric method in accordance with the present invention, since electron spin resonance and nuclear magnetic resonance can be caused at a common magnetic field intensity, nuclear magnetic resonance is usually caused immediately after excitement of electron spin (for instance, within one second).

The step (2) may be carried out immediately after the step (1) was carried out, or when a certain period of time passed after the step (1) was carried out, as long as the step (2) is carried out after the step (1) was carried out. A period of time after which the step (2) is to be carried out after the step (1) was carried out is arbitrarily determined in accordance with a purpose of measurement.

For instance, in the case that the target molecule having been accumulated in organ or tumor is to be measured, it is preferable that the step (2) is carried out after a sufficient period of time (for instance, an hour or longer) has lapsed in order to ensure the accumulation of the target molecule in organ or tumor.

The above-mentioned biometric method in accordance with the present invention can be applied to a diagnostic method. For instance, the biometric method in accordance with the present invention can be used in diagnosis such as MRI image diagnosis. As a concrete example, the biometric method in accordance with the present invention can be used for image diagnosis to malignant tumor such as cancer.

The biometric method in accordance with the present invention is explained hereinbelow in detail with reference to Table 1 and FIGS. 1 and 2.

First, hyperpolarization of nuclear spin is explained. A degree of hyperpolarization between nuclear spin and electron spin is dependent on a ratio in a gyromagnetic ratio between electron spin and nuclear spin. A gyromagnetic ratio of $e^-$ is 28 GHz/T, and a gyromagnetic ratio of $^{13}C$ is 10.7 MHz/T. Accordingly, maximum hyperpolarization is about 2600.

$$28 \text{ GHz}/T/10.7 \text{ MHz}/T \approx 2600$$

Next is explained signal amplification caused by measurement at a magnetic field intensity at which a nuclear magnetic resonance signal is degenerated, with reference to a schematic view of $^{13}C$-NMR spectrum.

FIG. 1(a) is a schematic view of $^{13}C$-NMR spectrum having been measured at a magnetic field intensity of 9.4 T. FIG. 1(b) is a schematic view having an axis of abscissa 100 times greater than the same in FIG. 1(a). FIG. 1(a) shows $^{13}C$-NMR spectrum in which two absorption spectral lines spaced away by 10 ppm from each other are observed. Though a width of each of the two absorption spectral lines is in the range of a few Hz to tens of Hz, a difference in frequency between the two absorption spectral lines is 1 kHz, and accordingly, the two absorption spectral lines do not overlap each other. That is, supposing that a signal intensity of each of the two signals is equal to one, signals each having a signal intensity of one are measured at different frequencies.

Figure 2:
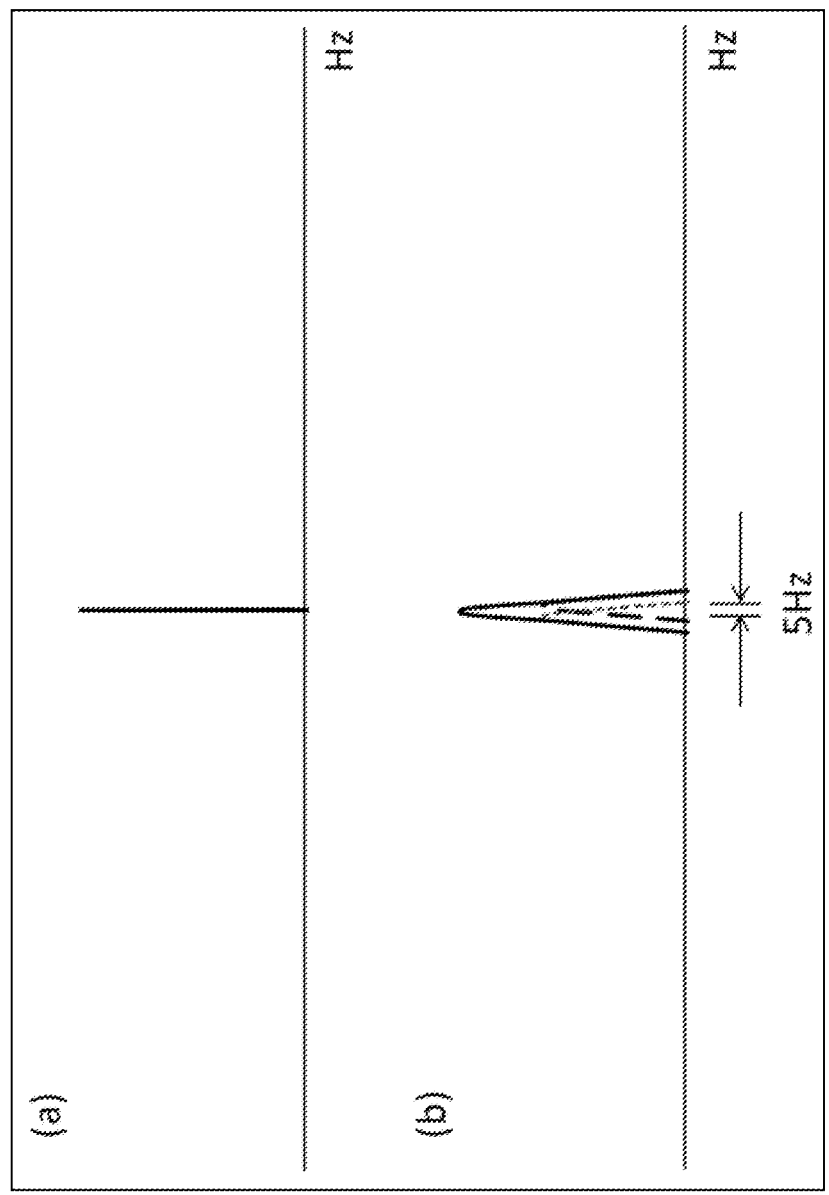
FIG. 2 includes schematic views of $^{13}C$-NMR spectrum (50 mT) to be used for explaining degeneration of nuclear magnetic resonance signals.

FIG. 2(a) is a schematic view of $^{13}C$-NMR spectrum having been measured at a magnetic field intensity of 50 mT with respect to the same sample as that of FIG. 1. FIG. 2(b) is a schematic view having an axis of abscissa 100 times greater than the same in FIG. 2(a). In the case that nuclear magnetic resonance of $^{13}C$ is measured at a magnetic field intensity of 50 mT, two signals each having an absorption line width in the range of a few Hz and tens of Hz and spaced away by 10 ppm from each other are detected, similarly to the measurement carried out at a magnetic field intensity of 9.4 T. However, since a difference in frequency between the two signals is 5 Hz, the two signals overlap each other into a single signal. Thus, the resultant spectrum includes a single absorption spectral line. Supposing each of the two signals has a signal intensity of 1 (one), since the two signals overlap each other into a single signal, a signal having a signal intensity almost twice greater than an intensity of a single signal is detected at a certain frequency.

As mentioned above, though a width of each of the absorption spectral lines is in the range of a few Hz to tens of Hz, the smaller a magnetic field intensity is, the smaller a difference in frequency between the two absorption spectral lines is, resulting in that the absorption spectral lines are compressed, and hence, the absorption spectral lines overlap each other. That is, a signal intensity is increased at a certain frequency.

Furthermore, degeneration of N absorption spectral lines is observed by setting a magnetic field intensity such that N absorption spectral lines are detected in a frequency band in the range of a few Hz to tens of Hz. Consequently, a signal intensity can be enhanced relative to two absorption spectral lines.

Table 1 shows the comparison in sensitivity between a case in which $^{13}C$ or a low gyromagnetic ratio nucleus present in target organism is measured in accordance with the biometric method in accordance with the present invention, and a case in which $^{13}C$ is measured in accordance with other methods. As can be understood in view of Table 1, a relative sensitivity to NMR at 50 mT is about 2600 times greater than other methods. Furthermore, since a signal intensity to be measured increases in proportion with a $^{13}C$ label number, an experimentally measured sensitivity is accordingly increased. Thus, the relative sensitivity surpasses the same to NMR measurement at 9.4 T.

TABLE 1

| Measurement system | X1 × X2 × X3 × X4 | Note |
|---|---|---|
| 50 mT $^{13}C$-NMR | 1 × 1 × n = n | Other method |
| 50 mT $^{13}C$-DNP | 2600 × 1 × n = 2600 × n | Present Invention |
| 9.4 T $^{13}C$-NMR | 188 × 13.7 × 1 = 2577 (9.4/50 mT) | Other method |

X1: sensitivity $T^{(1)}$ properties dependence
X2: $T^{(1/2)}$ measurement device dependence
X3: equivalent nuclear number
X4: relative sensitivity The biometric method in accordance with the present invention is explained hereinbelow in detail with reference to embodiments.

First Embodiment

In the step (1) in the first embodiment, a target molecule A1 is administered to target organism from the outside. At first, the target molecule A1 is administered to target organism such as human being or mouse by means of an injection.

The target molecule A1 comprises glucose derivative including glucose to which a radical molecule is bonded. The target molecule A1 includes six carbon atoms labelled with 13C in glucose part, and has accumulation characteristics to cancer cells. It is possible to estimate a distribution of accumulation of the target molecules A1 in organism by measuring $^{13}$C-NMR/MRI of the target molecules A1 in the step (2) mentioned later.

In step (2), the measurement is carried out to the target organism by means of an Overhauser-effect MRI apparatus. In the first embodiment, an OMRI apparatus illustrated in FIG. 3 is employed.

Figure 3:
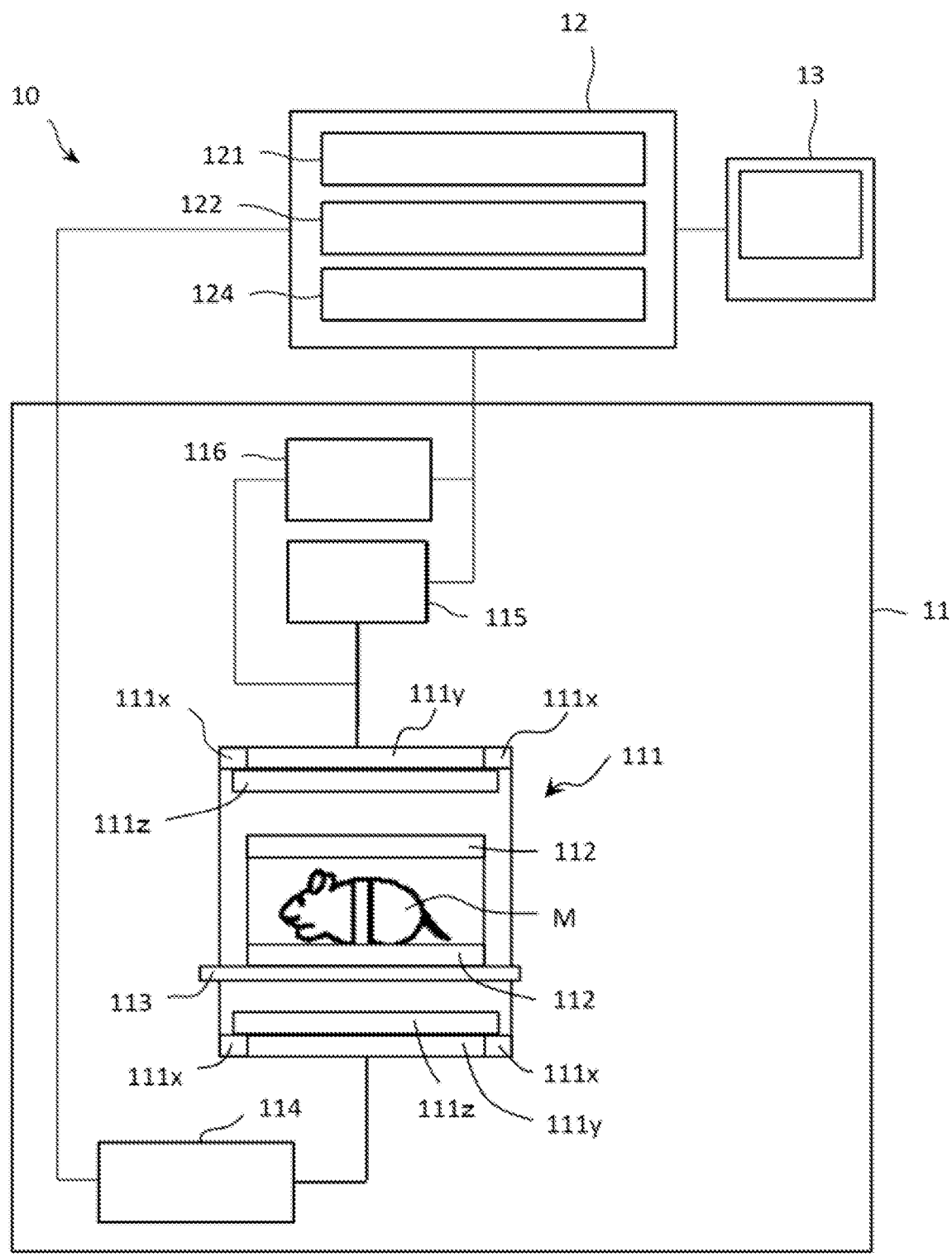
FIG. 3 is a block diagram of the OMRI apparatus to be used in the biometric method in accordance with the first and second embodiments.

A structure of the OMRI apparatus illustrated in FIG. 3 is explained hereinbelow with reference to the drawing.

The OMRI apparatus 10 illustrated in FIG. 3 measures organism as a target, and includes a main part 11 in which a target organism (a mouse M in the illustrated embodiment), a controller 12 for controlling operation of elements of the main part 11, and a display 13 for displaying results transmitted from the controller 12.

The main part 11 includes an external magnetic field generator 111 as a magnetic field generator for generating a low-intensity magnetic field having an intensity equal to or smaller than 50 mT, an RF coil (a resonator) 112 in which the target organism is enclosed, and a fixation stand 113 on which the RF coil 112 is fixed.

The external magnetic field generator 111 in the first embodiment includes an eternal magnet 111x, a magnetic field gradient coil 111y, and a magnetic field sweep coil 111z. The external magnetic field generator 111 provides excitation magnet field and measurement magnet field for OMRI.

The external magnetic field generator 111 is electrically connected to the controller 12 through a driver 114 which generates a static magnetic field. The static magnetic field generating driver 114 is electrically connected to a power source (not illustrated) for feeding power to both the magnetic field gradient coil lily and the magnetic field sweep coil 111z. The static magnetic field generating driver 114 controls both the magnetic field gradient coil lily and the magnetic field sweep coil 111z in accordance with commands received from the controller 12. The external magnetic field generator 111 in the first embodiment generates a magnetic field having an intensity of 20 mT. The intensity of a magnetic field generated by the external magnetic field generator 111 may be set to any intensity greater than 0, but equal to or smaller than 50 mT. An electromagnet may be used in place of the eternal magnet 111x.

Organism to be measured is kept in the RF coil 112. The RF coil 112 generates an electromagnetic wave magnetic field in a direction perpendicular to a static magnetic field generated by the external magnetic field generator 111.

The RF coil 112 is electrically connected to the controller 12 through a RF coil driver 115 and a detection signal receiver 116.

The RF coil driver 115 is electrically connected to a power source (not illustrated) for feeding power to the RF coil 112.

The RF coil driver 115 drives the RF coil 112 in accordance with sequence transmitted from the controller 12. When high frequency pulses are applied to the RF coil 112, a high frequency magnetic field is generated in the RF coil 112, and hence, organism as the target housed in the RF coil 112 is exposed to a high frequency magnetic field.

The RF coil 112 under the above-mentioned circumstance irradiates high frequency waves at a magnetic field intensity equal to or smaller than 50 mT in the external magnetic field generator 111. Thus, radicals (unpaired electrons) in the target molecule A1 having been administered to the target organism absorb the high frequency waves, and thus, electron spin is excited in resonance, resulting in that electron spin energy is transferred into nuclear spin by virtue of interaction between electron and nucleus. That is, nuclear spin is hyperpolarized.

The controller 12 includes a measurement sequence processor 121 receiving electron spin resonance signals and magnetic resonance signals from the target organism in accordance with measurement sequence, and an OMRI measurement processor 122.

The measurement sequence processor 121 includes a power-feeding sequence for both the external magnetic field generator 111 and the RF coil 112, and a measurement sequence for the RF coil 112 to thereby control both the external magnetic field generator 111 and the RF coil 112. The controller 12 is actually comprised of a computer system, and operates in the above-mentioned manner by executing a computer program stored in a recording medium such as a hard disc.

The OMRI measurement processor 122 processes images in accordance with both the electron spin resonance signals and the magnetic resonance signals having been obtained in accordance with the measurement sequence, to thereby obtain measurement image signals. A detection signal adjuster 124 adjusts the measurement image signals having been obtained by the OMRI measurement processor 122 to thereby obtain adjusted image signals in which influences caused by transfer are amended. The adjusted image signals obtained by the detection signal adjuster 124 are displayed in the display 13.

Hereinbelow is explained the step (2) to be carried out through the use of the above-mentioned OMRI apparatus 10 in accordance with the first embodiment of the present invention.

In the step (1), the target organism into which the target molecules A1 have been administered, for instance, the mouse M is housed in the RF coil 12 in the OMRI apparatus illustrated in FIG. 3.

In the first embodiment, the step (2) is carried out after a certain period of time has lapsed so as for the target molecules A1 to be able to accumulate in the target organism, subsequently to the step (1) in which the target molecules A1 were administered into the target organism.

Then, the RF coil 12 is driven to irradiate high frequency waves, and the magnetic field sweep coil 111z is driven in a magnetic field having an intensity of 20 mT in the external magnetic field generator 111, resulting in that a static magnetic field is swept at a high speed. Thus, unpaired electrons present in the target molecules A1 having been administered to the target organism absorb high frequency waves, and accordingly, electron spin is excited through resonance. At this time, electron spin having been excited through resonance is transferred into nuclear spin energy of $^{13}$C atoms existing in the target molecules A1, resulting in that nuclear spin is hyperpolarized. Then, signals transmitted from the target organism as a result of the irradiation of high frequency waves to the target organism are received at the detection signal receiver 116 by means of the RF coil 112. The signals detected in a region in which a difference in a chemical shift location of the target molecules A1 between a maximum and a minimum is equal to 50 ppm are observed only in a frequency band of 10 Hz, ensuring it possible to enhance an intensity of the received signals.

As mentioned above, the signals having been received at the detection signal receiver 116 are transmitted to the controller 12, and then, are processed in the OMRI measurement processor 122 to thereby synthesize images expressing MRI images and/or a distribution of nuclear spin.

Second Embodiment

In the second embodiment, there is used D-glucose (mixture of alpha and beta bodies), as a target molecule B1, including six carbon atoms labelled with $^{13}C$, and including no radicals. The radical molecule C has accumulation characteristics similarly to the target molecule B1.

In the step (1), both the target molecule B1 and the radical molecule C are administered into a target organism by means of an injection.

Then, in the step (2), nuclear magnetic resonance signals are measured from the target molecule B1 at a magnetic field intensity of 50 mT by means of the OMRI apparatus illustrated in FIG. 3, similarly to the first embodiment. In this measurement, since the $^{13}C$ signals transmitted from the target molecule B1 overlap with each other, the signals are measured with a signal intensity thereof being enhanced.

Figure 4:
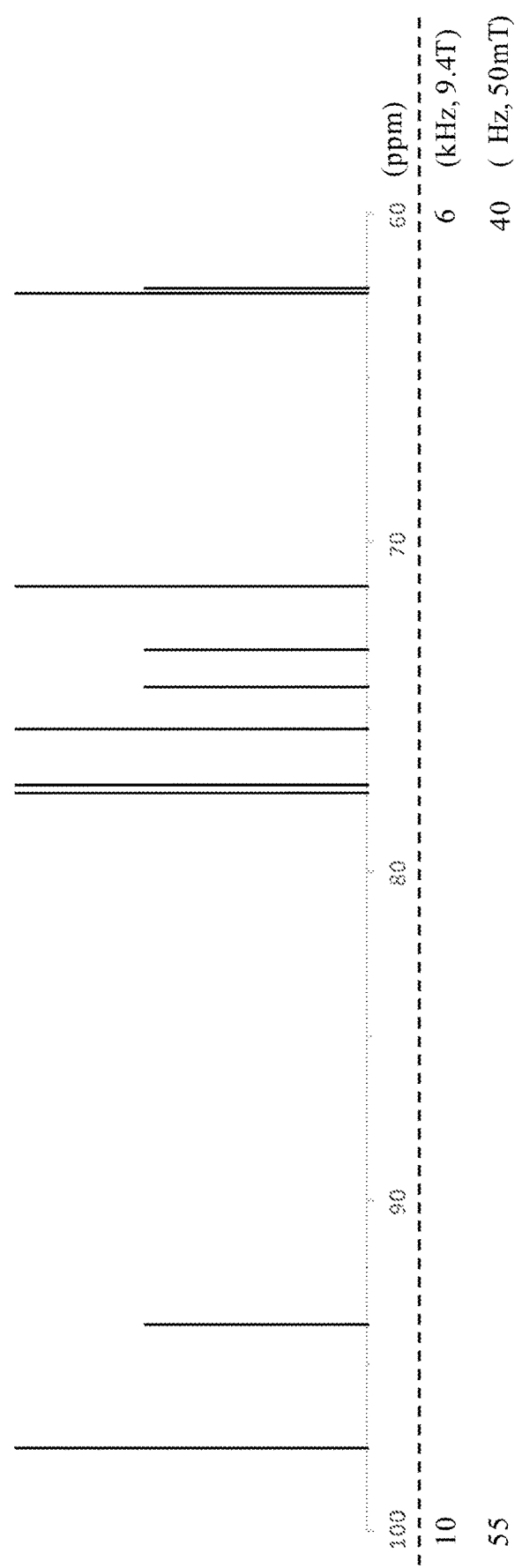
FIG. 4 is $^{13}C$-NMR simulation spectrum of D-glucose (mixture of alpha and beta forms).

Hereinbelow is explained amplification of a signal intensity of the signals received from the target molecule B1 with reference to $^{13}C$-NMR simulation spectrum of D-glucose (mixture of alpha and beta bodies). FIG. 4 shows $^{13}C$-NMR simulation spectrum of D-glucose (mixture of alpha and beta bodies). The illustrated $^{13}C$-NMR simulation spectrum is derived from six atoms in each of alpha and beta bodies. A label at an axis of abscissa indicates relative-value expression (ppm) and absolute-value expression (Hz, 9.4 T NMR, 50 mT OMRI). A width of each of absorption spectral lines is not taken into consideration.

A difference in chemical shift location between a maximum and a minimum is equal to 35 ppm in the $^{13}C$-NMR simulation spectrum of D-glucose (mixture of alpha and beta bodies). Considering experimental spectrum obtained by means of standard 9.4 T NMR (a frequency of electromagnetic wave is 100 MHz with respect to $^{13}C$) used for analysis, 1 ppm is equivalent to 100 Hz, and the difference in chemical shift location between a maximum and a minimum is equal to 3.5 kHz (expressed in a frequency, 100 Hz/ppm×35 ppm). A width of each of absorption spectral lines is in the range of a few Hz to tens of Hz, and the difference in chemical shift location between a maximum and a minimum is small relative to 3.5 kHz, and hence, the signals are divided.

Supposing that the measurement is carried out at a magnetic field intensity of 50 mT (a frequency of electromagnetic wave is 0.5 MHz with respect to $^{13}C$), the difference in chemical shift location between a maximum and a minimum is equal to about 15 Hz (expressed in a frequency, 0.5 Hz/ppm×35 ppm). The difference in chemical shift location between a maximum and a minimum is observed in a compressed band, specifically, in a frequency band of 15 Hz. A width of each of absorption spectral lines is in the range of a few Hz to tens of Hz, and thus, $^{13}C$-NMR spectrums of D-glucose are observed in such a condition that they overlap with each other.

As mentioned above, the biometric method in accordance with the embodiments of the present invention makes it possible to measure low-sensitivity magnetic resonance nucleus such as $^{13}C$, $^{15}N$, and $^{31}P$, which are important nuclides present in organism, with performance equal to or over that of a high-field NMR device.

INDUSTRIAL APPLICABILITY

The biometric method in accordance with the present invention makes it possible to carry out molecular dynamic imaging by using labels such as $^{13}C$ and $^{15}N$, which are important nuclides present in organism, as molecular probes. Consequently, it is quite useful for analysis of physiological function and pharmacokinetics to carry out measurement and imaging of distribution and metabolism of organism by means of the biometric method and apparatus in accordance with the present invention.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

The invention claimed is:

1. A biometric method including:
   a step (1) for administering, to a target organism from the outside thereof, one of (i) a target molecule A having both an unpaired electron and a magnetic resonance nucleus having a gyromagnetic ratio smaller than the same of $^{19}F$, and (ii) a target molecule B and a radical molecule C, the target molecule B having no unpaired electron, and further having a magnetic resonance nucleus having a gyromagnetic ratio smaller than the same of $^{19}F$, the radical molecule C having an unpaired electron; and
   a step (2) for causing electron spin resonance in the unpaired electron of the target molecule A or the radical molecule C by irradiating electromagnetic waves to the target organism, subsequently triggering nuclear magnetic resonance in the magnetic resonance nucleus having a gyromagnetic ratio smaller than the same of $^{19}F$ in one of the target molecule A and the target molecule B, and further, measuring nuclear magnetic resonance signals,
   the step (2) being carried out in a magnetic field having such an intensity that the nuclear magnetic resonance signals of the magnetic resonance nucleus in one of the target molecule A and the target molecule B are degenerated, the magnetic resonance nucleus having a gyromagnetic ratio smaller than the same of $^{19}F$.

2. The biometric method as set forth in claim 1, wherein the magnetic resonance nucleus comprises one of $^{13}C$, $^{14}N$, $^{15}N$, and $^{31}P$.

3. The biometric method as set forth in claim 1, wherein the step (2) is carried out in a magnetic field having an intensity equal to or smaller than 50 mT.

4. The biometric method as set forth in claim 1, wherein the step (2) is carried out in a magnetic field having a constant intensity.

5. The biometric method as set forth in claim 1, wherein one of the target molecule A and the target molecule B includes two or more magnetic resonance nuclei having a gyromagnetic ratio smaller than the same of $^{19}F$.

6. The biometric method as set forth in claim 1, wherein one of the target molecule A and the target molecule B has accumulation characteristics to tumor.

7. The biometric method as set forth in claim 1, wherein one of the target molecule A and the target molecule B comprises glucose derivative.

8. A biometric apparatus including:
   a first device for administering, to a target organism from the outside thereof, one of (i) a target molecule A having both an unpaired electron and a magnetic resonance nucleus having a gyromagnetic ratio smaller than the same of $^{19}F$, and (ii) a target molecule B and a radical molecule C, the target molecule B having no unpaired electron, and further having a magnetic resonance nucleus having a gyromagnetic ratio smaller than the same of $^{19}$F, the radical molecule C having an unpaired electron; and a second device for causing electron spin resonance in the unpaired electron of the target molecule A or the radical molecule C by irradiating electromagnetic waves to the target organism, subsequently triggering nuclear magnetic resonance in the magnetic resonance nucleus having a gyromagnetic ratio smaller than the same of $^{19}$F in one of the target molecule A and the target molecule B, and further, measuring nuclear magnetic resonance signals, the second device measuring the nuclear magnetic resonance signals in a magnetic field having such an intensity that the nuclear magnetic resonance signals of the magnetic resonance nucleus in one of the target molecule A and the target molecule B are degenerated, the magnetic resonance nucleus having a gyromagnetic ratio smaller than the same of $^{19}$F.

9. The biometric apparatus as set forth in claim 8, wherein the magnetic resonance nucleus comprises one of $^{13}$C, $^{14}$N, $^{15}$N, and $^{31}$P.

10. The biometric apparatus as set forth in claim 8, wherein the second device measures the nuclear magnetic resonance signals in a magnetic field having an intensity equal to or smaller than 50 mT.

11. The biometric apparatus as set forth in claim 8, wherein the second device measures the nuclear magnetic resonance signals in a magnetic field having a constant intensity.

12. The biometric apparatus as set forth in claim 8, wherein one of the target molecule A and the target molecule B includes two or more magnetic resonance nuclei having a gyromagnetic ratio smaller than the same of $^{19}$F.

13. The biometric apparatus as set forth in claim 8, wherein one of the target molecule A and the target molecule B has accumulation characteristics to tumor.

14. The biometric apparatus as set forth in claim 8, wherein one of the target molecule A and the target molecule B comprises glucose derivative.

15. A non-transitory recording medium readable by a computer, storing a program therein for causing a computer to carry out a biometric method in a biometric apparatus, the method including:

a step (1) for administering, to a target organism from the outside thereof, one of (i) a target molecule A having both an unpaired electron and a magnetic resonance nucleus having a gyromagnetic ratio smaller than the same of $^{19}$F, and (ii) a target molecule B and a radical molecule C, the target molecule B having no unpaired electron, and further having a magnetic resonance nucleus having a gyromagnetic ratio smaller than the same of $^{19}$F, the radical molecule C having an unpaired electron; and a step (2) for causing electron spin resonance in the unpaired electron of the target molecule A or the radical molecule C by irradiating electromagnetic waves to the target organism, subsequently triggering nuclear magnetic resonance in the magnetic resonance nucleus having a gyromagnetic ratio smaller than the same of $^{19}$F in one of the target molecule A and the target molecule B, and further, measuring nuclear magnetic resonance signals, the step (2) being carried out in a magnetic field having such an intensity that the nuclear magnetic resonance signals of the magnetic resonance nucleus in one of the target molecule A and the target molecule B are degenerated, the magnetic resonance nucleus having a gyromagnetic ratio smaller than the same of $^{19}$F.

16. The non-transitory recording medium as set forth in claim 15, wherein the step (2) is carried out in a magnetic field having an intensity equal to or smaller than 50 mT.

17. The non-transitory recording medium as set forth in claim 15, wherein the step (2) is carried out in a magnetic field having a constant intensity.

\* \* \* \* \*